United States Patent [19]
Hasegawa et al.

[11] Patent Number: 4,605,622
[45] Date of Patent: Aug. 12, 1986

[54] PROCESS FOR PRODUCING GRANULAR FIXED ENZYMES OR MICROORGANISMS
[75] Inventors: Eiichi Hasegawa; Takamitsu Iida; Masahiro Sakamoto, all of Hiratsuka, Japan
[73] Assignee: Kansai Paint Co., Ltd., Hyogo, Japan
[21] Appl. No.: 551,928
[22] Filed: Nov. 15, 1983
[51] Int. Cl.⁴ .................. C12N 11/04; C12N 11/02; C12N 11/10; C12N 11/12
[52] U.S. Cl. .................. 435/182; 435/177; 435/178; 435/179
[58] Field of Search ............ 435/174, 177, 178, 179, 435/182

[56] References Cited
U.S. PATENT DOCUMENTS

| | | | |
|---|---|---|---|
| 4,138,292 | 2/1979 | Chibata et al. | 435/178 |
| 4,195,129 | 3/1980 | Fukui et al. | 435/182 |
| 4,334,027 | 6/1982 | Klein et al. | 435/182 X |
| 4,338,401 | 7/1982 | Cremonesi | 435/182 X |
| 4,347,320 | 8/1982 | Borglum | 435/182 X |
| 4,350,765 | 9/1982 | Chibata et al. | 435/182 X |
| 4,546,081 | 10/1985 | Yamada et al. | 435/182 X |

Primary Examiner—David M. Naff
Attorney, Agent, or Firm—Wenderoth, Lind & Ponack

[57] ABSTRACT

A granular fixed molded article of an enzyme or microorganism strain is prepared by adding dropwise a liquid composition, composed of (a) a hydrophilic photocurable resin having at least two ethylenically unsaturated bonds per molecule, (b) a photopolymerization initiator, (c) a water-soluble high-molecular-weight polysaccharide having the ability to become a gel upon contact with at least one polyvalent metal ion and (d) an enzyme or microorganism strain, to an aqueous medium containing a polyvalent metal ion to gel the composition in a granular form, and then irradiating actinic light on the resulting granular gel to cure the photocurable resin in the granular gel.

12 Claims, No Drawings

PROCESS FOR PRODUCING GRANULAR FIXED ENZYMES OR MICROORGANISMS

This invention relates to a process for fixing an enzyme or microorganism strain, and more specifically, to a process for fixing an enzyme or microorganism strain as a granular molded article.

Many methods such as entrapping, physical adsorption or covalent bonding have been known heretofore for the fixation of enzymes or microorganisms. In using a fixed product in the form of a mass or sheet obtained by such methods in a microorganism reaction, it is the usual practice to fill it in a column after it has been cut or crushed finely. Since, however, the fixed product frequently undergoes intimate surface-to-surface contact, the efficiency of the microorganism reaction is reduced, or frequently a channeling phenomenon occurs to block up the column.

The present inventors thought that if an enzyme or microorganism strain can be fixed as a granular molded article, it would become easy to fill the fixed product into a column because of its good flowability, the area of contact between the granules would be small and the efficiency of the microorganism reaction could be increased. Based on this thought, they undertook extensive investigations about the method of fixing enzymes or microorganism strains as granular articles. These investigations have led to the discovery that if a combination of a certain kind of hydrophilic photocurable resin and a water-soluble high-molecular-weight polysaccharide having the ability to become a gel upon contact with a polyvalent metal ion is used as a carrier for fixation, a granular fixed article of an enzyme or microorganism strain having high mechanical strength can be produced very easily in an aqueous medium without loss of the enzyme or microorganism strain.

Thus, according to this invention, there is provided a process for producing a granular fixed molded article of an enzyme or microorganism strain, which comprises adding dropwise a liquid composition composed of (a) a hydrophilic photocurable resin having at least two ethylenically unsaturated bonds per molecule, (b) a photopolymerization initiator, (c) a water-soluble high-molecular-weight polysaccharide having the ability to become a gel upon contact with a polyvalent metal ion and (d) an enzyme or microorganism strain to an aqueous medium containing a polyvalent metal ion to gel the composition in a granular form, and then irradiating actinic light on the resulting granular gel to cure the photocurable resin in the granular gel.

The process of this invention will be described below in detail.

(a) Hydrophilic photocurable resin

In the process of this invention, a hydrophilic photocurable resin having at least two ethylenically unsaturated bonds per molecule is used as one fixation carrier. Suitable hydrophilic photocurable resins for use in this invention may have a number average molecular weight of generally 300 to 100,000, preferably 500 to 20,000, contain an ionic or nonionic hydrophilic group, such as a hydroxyl group, a carboxyl group, a phosphoric acid group, a sulfonic acid group, an amino group or an ether linkage, which is sufficient for the hydrophilic photocurable resin to disperse uniformly in an aqueous medium having an enzyme or microorganism strain suspended therein, and when exposed to irradiation of actinic light having a wavelength of about 250 to about 600 nm, preferably about 300 to about 400 nm, are cured to substantially water-insoluble solid resins. Such photocurable resins have already been known per se as carriers for fixation of enzymes or microorganism strains (for example, see U.S. Pat. No. 4,195,129 and British Pat. Nos. 1,550,465 and 1,550,151). Typical examples are shown below.

(i) Unsaturated polyesters having a high acid value

Salts of unsaturated polyesters having an acid value of 40 to 200, preferably 50 to 100, obtained by the esterification of a polyhydric alcohol with a polycarboxylic acid component selected from the group consisting of at least one unsaturated polycarboxylic acid such as maleic anhydride, maleic acid, fumaric acid, itaconic acid or itaconic anhydride and at least one saturated polycarboxylic acid such as trimellitic acid, trimellitic anhydride, pyromellitic acid or pyromellitic anhydride; and unsaturated polyesters having an acid value of 40 to 200, preferably 50 to 100, obtained by reacting an acid anhydride with the residual hydroxyl groups of an esterification product between at least one unsaturated carboxylic acid such as maleic anhydride, maleic acid, fumaric acid, itaconic acid or itaconic anhydride and a polyhydric alcohol component containing at least 5% by weight of a polyhydric alcohol having more than 3 hydroxyl groups per molecule.

(ii) Unsaturated epoxides having a high acid value

Unsaturated epoxides having an acid value of 40 to 200, preferably 50 to 100, obtained by the addition of an acid anhydride to the residual hydroxyl groups of an adduct of n moles of a polyglycidyl compound such as Epikote 828, Epikote 1001 and Epikote 1004 of Shell Chemical Co., (n−1) moles of a polycarboxylic acid such as maleic acid, adipic acid or trimellitic acid and 2 moles of an unsaturated carboxyl compound such as (meth)acrylic acid; and unsaturated epoxides having an acid value of 40 to 200, preferably 50 to 100, obtained by adding an acid anhydride to the residual hydroxyl groups of an adduct of n moles of the aforesaid polyglycidyl compound and (n+2) moles of the aforesaid polycarboxylic acid, and further reacting the resulting adduct with an unsaturated glycidyl compound such as glycidyl (meth)acrylate.

(iii) Anionic unsaturated acrylic resins

The anionic unsaturated acrylic resins denote resins which are obtained by introducing a photopolymerizable ethylenically unsaturated group into a copolymer having a carboxyl group, a phosphoric acid group and/or a sulfonic acid group obtained by copolymerizing at least two (meth)acrylic monomers selected from (meth)acrylic acid and (meth)acrylic acid esters and have an A value, calculated by the following equation, of 0.8 to 5, preferably 1 to 3, moles/kg, $$C + 5P + 10S = A \quad \ldots \quad (1)$$

wherein C is the concentration (moles/kg of resin) of the carboxyl groups in the resin, P is the concentration (moles/kg of resin) of the phosphoric acid groups in the resin, and S is the concentration (mole/kg of resin) of the sulfonic acid groups in the resin, and in which the concentration of the photopolymerizable ethylenically unsaturated group in the resin is in the range of from 0.1 to 5, preferably from 1 to 3, moles/kg of resin. Such a copolymer can be synthesized by methods known per se. Copolymers having a carboxyl group can be obtained if an unsaturated carboxylic acid such as acrylic acid or methacrylic acid is used as a comonomer. Copolymers having a phosphoric acid group can be obtained if an unsaturated phosphoric acid ester such as Phosmer M or Phosmer Cl (both tradenames for products supplied by Yushi Seihin K.K.) is used as a comonomer. Furthermore, copolymers having a sulfonic acid group can be obtained if an unsaturated sulfonic acid ester such as 2-sulfoethyl (meth)acrylate or 3-sulfopropyl (meth)acrylate is used as a comonomer. A photopolymerizable ethylenically unsaturated group can be introduced into the resulting copolymer by reacting an unsaturated glycidyl compound such as glycidyl (meth)acrylate with the carboxyl, phosphoric acid or sulfonic acid group present in the copolymer.

(iv) Cationic unsaturated acrylic resins

Unsaturated acrylic resins obtained by reacting a copolymer of a (meth)acrylic acid ester containing more than 5% by weight of a comonomer unit derived from unsaturated amino compounds such as 2-diethylaminoethyl (meth)acrylate, tert-butylaminoethyl (meth)acrylate or vinylpyridine, with an unsaturated glycidyl compound such as glycidyl (meth)acrylate; unsaturated acrylic resins obtained by chloromethylating polystyrene and then quaternizing the product with unsaturated amino compounds; and adducts of polyethyleneimine and unsaturated glycidyl compounds.

(v) Polyesters of polyethylene glycols and (meth)acrylic acid

Diesters of unsaturated monocarboxylic acids such as (meth)acrylic acid with polyethylene glycols having a molecular weight of 400 to 10,000, preferably 400 to 6,000, and containing less than 30% by weight of a propylene oxide unit; esterification products of n moles of dibasic acids such as maleic anhydride, (n+1) moles of polyethylene glycol having a molecular weight of 400 to 10,000, preferably 400 to 6,000, and 2 moles of unsaturated monocarboxylic acids such as (meth)acrylic acid; and esterification products of n moles of tribasic acids such as trimellitic acid, (n+2) moles of polyethylene glycol having a molecular weight of 400 to 10,000, preferably 400 to 6,000, and 3 moles of unsaturated carboxylic acid such as (meth)acrylic acid.

(vi) Urethanization adducts of polyethylene glycols and 2-hydroxyethyl (meth)acrylate Urethanization products of n moles of diisocyanates such as tolylene diisocyanate, xylylene diisocyanate or hexamethylene diisocyanate, (n-1) moles of polyethylene glycol having a molecular weight of 400 to 10,000, preferably 400 to 6,000, and 2 moles of unsaturated monohydroxy compounds such as 2-hydroxyethyl (meth)acrylate; urethanization products of n moles of triisocyanates such as Desmodur L (a product of Bayer AG), (n−1) moles of polyethylene glycol having a molecular weight of 400 to 10,000, preferably 400 to 6,000, and (n+2) moles of unsaturated monohydroxy compounds such as 2-hydroxyethyl (meth)acrylate; and urethanization products of 1 mole of trifunctional hydroxy compounds such as trimethylolpropane, 4 moles of diisocyanates, 2 moles of polyethylene glycols having a molecular weight of 400 to 10,000, preferably 400 to 6,0000, and 2 moles of unsaturated monohydroxy compounds such as 2-hydroxyethyl (meth)acrylate.

(vii) Unsaturated celluloses

Adducts formed between water-soluble cellulose derivatives such as cellulose acetate phthalate, hydroxypropyl methyl cellulose phthalate and hydroxyethyl cellulose and unsaturated glycidyl compounds such as glycidyl (meth)acrylate or unsaturated acid anhydrides such as itaconic anhydride or maleic anhydride.

(viii) Unsaturated polyamides

Unsaturated polyamides obtained by subjecting adducts between 1 mole of diisocyanates such as tolylene diisocyanate and xylylene diisocyanate and 1 mole of unsaturated hydroxy compounds such as 2-hydroxyethyl acrylate to an addition reaction with water-soluble polyamides such as gelatin.

The above-exemplified photocurable resins can be used singly or in combination with each other. Among the above photocurable resins, the polyesters of polyethylene glycols and (meth)acrylic acid exemplified under (v) and the urethanization adducts of polyethylene glycols and 2-hydroxyethyl (meth)acrylate exemplified under (vi) can be especially advantageously used in this invention.

(b) Photopolymerization initiator

In order to promote the photopolymerization reaction of the photocurable resin (a) described above, a photopolymerization initiator (photosensitizer) is included in the liquid composition used in this invention. Usable photopolymerization initiators are those capable of yielding radicals upon decomposition by light irradiation, which radicals become polymerization initiating species and induce crosslinking reaction between resins having a polymerizable unsaturated group. Specific examples include alphacarbonyl alcohols such as benzoin and acetoin; acyloin ethers such as benzoin methyl ether, benzoin ethyl ether, benzoin propyl ether, anisoin ethyl ether and pivaloin ethyl ether; polynuclear aromatic compounds such as naphthol and hydroxyanthracene; alpha-substituted acyloins such as methylbenzoin and alpha-methoxYbenzoin; azoamide compounds such as 2-cyano-2-butylazoformamide; metal salts such as uranyl nitrate and ferric chloride; mercaptans; disulfides; halogen compounds; and dyes.

These photopolymerization initiators may be used singly or in combination with each other in an amount of usually 0.01 to 100, preferably 0.1 to 5, PHR (per hundred resin).

(c) Water-soluble high-molecular-weight polysacchrides

One great characteristic of this invention is to use a water-soluble high-molecular-weight polysaccharide in combination with the photocurable resin (a), as a fixation carrier.

Suitable water-soluble high-molecular-weight polysaccharides which can be used in this invention have the ability to change to water-insoluble or sparingly water-soluble gels upon contact with a polyvalent metal ion in an aqueous medium. They have a molecular weight of generally about 3,000 to about 2,000,000, preferably about 100,000 to about 1,000,000, and in its water-soluble form before contact with a polyvalent metal ion, show a water solubility of usually at least about 10 g/liter (at 25° C.), preferably at least least 30 g/liter (at 25° C.)

Specific examples of the water-soluble high-molecular weight polysaccharide having such characteristics include alkali metal salts of alginic acid, carrageenan, konjac mannan, and pectin.

The water-soluble high-molecular-weight polysaccharide can be gelled when in the state of being dissolved in an aqueous medium, it contacts a polyvalent metal ion, for example at least one polyvalent metal ion selected from alkaline earth metal ions such as magnesium, calcium, strontium, and barium ions and other polyvalent metal ions such as cerium and nickel ions. It is not necesssary for the water-soluble high-molecular-weight polysaccharide to have the ability to become a gel upon contact with all polyvalent metal ions. All that is sufficient is that it should have the ability to become a gel when brought into contact with at least one polyvalent metal ion, preferably an alkaline earth metal ion. The concentration of the polyvalent metal ion at which gellation occurs differs depending upon the kind of the water-soluble high-molecular-weight polysacharide, but is generally at least 0.01 mole/liter, preferably 0.1 to 2 moles/liter.

(d) Enzymes or microorganism strains

There is no particular restriction of the kind of the enzyme or microorganism strain which can be fixed by the process of this invention. According to the process of this invention, any kinds of enzymes or microorganism strains can be fixed without substantially depriving them of their enzymatic activity or fermenting ability.

Typical examples of enzymes and microorganism strains which can be fixed by the process of this invention are given below.

(A) Enzymes
Lactate dehydrogenase (1.1.2.3),
lactate oxidase (1.1.3.2),
glucose oxidase (1.1.3.4),
formate dehydrogenase (1.2.1.2),
aldehyde dehydrogenase (1.2.2.3),
aldehyde oxidase (1.2.3.1),
xanthine oxidase (1.2.3.2),
pyruvate oxidase (1.2.3.3),
pyruvate reductase (1.2.4.1),
cortisone-alpha-reductase (1.3.1.4),
acyl CoA-dehydrogenase (13.99.3),
3-ketosteroid $\Delta^1$-dehydrogenase,
3-ketosteroid $\Delta^4$-dehydrogenase (1.3.99.5),
L-alanine dehydrogenase (1.4.1.1),
L-glutamic acid dehydrogenase (1.4.1.3),
L-amino acid oxidase (1.4.3.2),
D-amino acid oxidase (1.4.3.3),
pyridoxal phosphate oxidase (I1.4.3.5),
catalase (1.11.1.6),
catechol methyltransferase (2.1.1.6),
carnitine acetyltransferase (2.3.1.7),
acetyl CoA acetyltransferase (2.3.1.9),
aspartate aminotransferase (2.6.1.1),
alanineaminotransferase (2.6.1.2),
pyridoxamine pyruvate transferase (2.6.1),
hexokinase (2.7.11),
glucokinase (2.7.1.2),
fructokinase (2.7.1.4),
phosphoglucokinase (2.7.1.10),
phosphofructokinase (2.7.1.11),
pyruvate kinase (I2.7.1.40),
carboxyesterase (3.1.1.1),
arylesterase (3.1.1.2),
lipase (3.1.1.3),
phospholipase A (3.1.1.4),
acetylesterase (3.1.1.6),
cholesterol esterase (3.1.1.13),
glucoamylase (3.2.1.3),
cellulase (3.2.1.4),
inulase (3.2.1.7),
alpha-glucosidase (3.2.1.20),
beta-glucosidase (3.2.1.21),
alpha-galactosidase (3.2.1.22),
beta-galactosidase (3.2.1.23),
invertase (3.2.1.26),
pepsin (3.4.4.1),
trypsin (3.4.4.4),
chymotrypsin A (3.4.4.5),
cathepsin A (3.4),
papain (3.4.4.10),
thrombin (3.4.4.13),
amidase (3.5.1.4),
urease (3.5.1.5),
penicillin acylase (3.5.1.11),
aminoacylase (3.5.1.14),
adenine deaminase (3.5.4.2),
ATPase (3.6.1.3),
pyruvate decarboxylase (4.1.1.1),
oxalate decarboxylate (4.1.1.2),
tryptophan decarboxylase (4.1.1.27),
aldolase (4.1.2.13),
malate synthase (4.1.3.2),
tryptophan synthase (4.2.1.20),
aspartase (4.3.1.1),
lysine racemase (5.1.1.5),
glucose-6-phosphate isomerase (5.3.1.9), and
steroid $\Delta$-isomerase (5.3.3.1).

(The parenthesized figures show enzyme numbers.)

(B) Microorganism strains
Bacteria
*Lactobacillus bulgaricus* ATCC 11842,
*Aerobacter aerogenes* ATCC 13048,
*Bacillus subtilis* ATCC 9799,
*Azotobacter vinelandii* ATCC 12837,
*Proteus vulgaris* ATCC 6059,
*Arthrobacter simplex* ATCC 6946,
*Escherichia coli* ATCC 15223,
*Pseudomonas putida* ATCC 12633,
*Achromobacter liquidum* ATCC 25311, and
*Nocardia rhoderous* NCIB 10554.

Fungi and Yeasts
*Curvularia lunata* ATCC 12017,
*Saccharomyces formosensis* IFO 0216,
*Saccharomyces cerevisiae* ATCC 10275,
*Saccharomyces carlsbergensis* ATCC 9080,
*Saccharomyces robustus* IFO 0224,
*Saccharomyces rouxii* ATCC 2615,
*Zygosaccharomyces japonicus* ATCC 11069,
*Zygosaccharomyces majar,*
*Zygosaccharomyces soya,*
*Schizosaccharomyces pombe* ATCC 2476,
*Schizosaccharomyces octosporus* (ATCC 2479), and
*Schizosaccharomyces mellacei.*

These enzymes and microorganisms may be used singly or as a mixture of two or more. If desired, they may be individually fixed so that two or more fixed products are used simultaneously.

For practical purposes, yeasts having the ability to ferment alcohols are of particular interest among the above-exemplified enzymes and microorganism strains.

Preparation of a liquid composition

A liquid composition may be formed by thoroughly mixing the components (a), (b), (c) and (d) in an aqueous medium. Water or an aqueous buffer solution is suitable as the aqueous medium. If desired, a mixture of a water-soluble alcohol with water or an aqueous buffer solution, a mixture of a water-soluble ketone with water or an aqueous buffer solution, or a solution of an ester-type solvent which is uniformly miscible with water or an aqueous buffer solution may also be used.

The proportions of the components (a), (b), (c) and (d) are not strictly limited, and can be varied widely according to the types of the individual components, etc. Generally, per 100 parts by weight of the hydrophilic photocurable resin (a), the components (b), (c) and (d) may be used in the following proportions (the parenthesized figures show preferred ranges).

(b) Photopolymerization initiator 0.01 to 10 parts by weight (0.1 to 5 parts by weight)
(c) Water-soluble high-molecular-weight polysaccharide 0.5 to 15 parts by weight (1 to 8 parts by weight)
(d) Enzyme or microorganism strain 0.001 to 50 parts by weight (0.01 to 20 parts by weight).

The aqueous medium may be used in an amount of 10 to 1,500 parts by weight, preferably 50 to 900 parts by weight, based on the total weight of the above components (a) to (d).

Gellation

The liquid composition prepared as above is then added dropwise to an aqueous medium containing a polvalent metal ion to gel it in a granular form.

The polyvalent metal ion to be included in the aqueous medium is selected from those which have the ability to gel the aqueous high-molecular-weight polysaccharide in the liquid composition. Whether the polyvalent metal ion has the ability to gel the water-soluble high-molecular-weight polysaccharide can be easily determined by adding a uniform mixed aqueous solution containing the hydrophilic photocurable resin and the water-soluble high-molecular-weight poysaccharide dropwise to an aqueous solution containing the polyvalent metal ion and observing the mixture to determine whether a granular gel is formed or not.

The aqueous medium containing the selected polyvalent metal ion can be prepared by dissolving a water-soluble compound of the polyvalent metal such as a halide, carbonate, bicarbonate, sulfate or nitrate of the polyvalent metal in the aqueous medium. The concentration of the polyvalent metal ion in the aqueous medium can be adjusted generally to 0.01 to 5 moles/liter, preferably 0.1 to 2 moles/liter.

The dropwise addition of the liquid composition to the aqueous medium containing the polyvalent metal ion can be carried out, for example, by adding dropwise the liquid composition from the tip of a slender tube such as a syringe, or scattering the liquid composition in granular form by utilizing centrifugal force, or by atomizing the liquid composition from the tip of a nozzle and thus adding it dropwise in granular form. The size of the liquid droplets to be added dropwise can be freely changed according to the desired particle size of the final granular fixed product to be obtained. Usually, it is convenient to add dropwise liquid droplets having a diameter of about 0.1 to about 5 mm, preferably about 0.5 to about 3 mm.

The added liquid composition contacts the polyvalent metal ion in the aqueous medium and is instantly gelled to become a granular gel. The mechanism of gellation at this time has not been elucidated definitely. It is presumed however that the water-soluble high-molecular-weight polysaccharide is flocculated by a halide or a salt solution and then the anionic group contained in the water-soluble high-molecular-weight polysaccharide is ionically bonded through the polyvalent metal ion whereby the polysaccharide is three-dimensionally crosslinked to form a gel.

Usually, room temperature suffices as the temperature of gellation. If desired, the gellation may be carried out at a temperature at which the enzyme or microorganism strain is not deactivated. Alternatively, the gellation may be carried out under cooling.

Photocuring

The granular gel formed as above is exposed to irradiation of actinic light either as dispersed in the aqueous medium or after it has been separated from the aqueous medium, thereby curing the hydrophilic photocurable resin in the granular gel. As a result, a granular fixed product of the enzyme or microorganism strain which is substantially water-insoluble and has high mechanical strength can be obtained.

The wavelength of the actinic light used in the photocuring reaction varies depending upon the type of the photocurable resin included in the gel. Generally, it is advantageous to use a light source which emits light having a wavelength in the range of about 250 to about 600 nm, preferably 300 to 400 nm. Examples of such a light source include a low-pressure mercury lamp, a high-pressure mercury lamp, a xenon lamp, a carbon arc lamp and sunlight. The irradiation time should be changed depending upon the intensity of the light from the light source, the distance from the light source, etc. Generally, it may be within the range of about 0.5 to about 10 minutes. The irradiation time may sometimes be shortened if the irradiation is carried out in an inert atmosphere.

The irradiation must be carried out so that the actinic light can reach the entire granular gel as uniformly as possible. For example, in the case of irradiating actinic light on the granular gel separated from the aqueous medium, it is convenient to place the separated granular gel in a suitable transparent glass plate or glass container so that it substantially forms a single layer, and to irradiate actinic light from both below and above the glass plate or glass container.

Room temperature also suffices as the temperature at which the granular gel is photocured. If desired, the irradiation can be carried out at an elevated temperature at which the enzyme or microorganism strain is not deactivated. Alternatively, the irradiation may be carried out under cooling.

The granular gel which has been exposed to irradiation is washed with water or an aqueous buffer solution, and then stored as such or after it is lyophilized.

Thus, according to the process of this invention, a granular fixed product of an enzyme or microorganism strain which has a particle diameter of about 0.5 to about 5 mm can be produced by a very simple operation, and continuous production is also possible.

The present invention brings about various advantages. For example, the invention makes possible the production of a granular fixed product of an enzyme or micoorganism strain by using a synthetic carrier, which has heretofore been difficult. The use of the water-soluble high-molecular-weight polysaccharide produces an effect of protecting the activity of the enzyme or microorganism strain. Furthermore, when the resulting granular fixed product is used, the water-soluble high-molecular-weight polysaccharide is gradually peptized and escapes from the photocurable resin matrix to leave fine pores in the fixed product. These fine pores increase the permeation of a substrate into the fixed product, and lead to an increase in the rate of the reaction.

These granular fixed products obtained by this invention can be conveniently used particularly in reactors whose scale is not so large, or in fluidized bed-type reactors.

The following Examples illustrate the present invention further.

EXAMPLE 1

One hundred parts by weight of a photocurable prepolymer composed of 2,000 g of polyethylene glycol having a molecular weight of about 4,000, 222 g (1 mole) of isophorone diisocyanate and 130 g (1 mole) of 2-hydroxyethyl methacrylate, 2 parts by weight of benzoin isobutyl ether and 100 parts by weight of distilled water were well mixed. To the mixture were added 100 parts by weight of a 2% aqueous solution of sodium alginate and 100 parts by weight of a suspension (concentration 10%) of *Saccharomyces cervisiae* (ATCC 11909) were added, and these materials were thoroughly mixed. The resulting mixture of the photocurable resin and the yeast was added dropwise to a 1M solution of calcium chloride from an injection syringe at a height 10 cm above the liquid surface. There was obtained a granular product having a particle size of about 2 mm.

The granular product was placed in a Petri dish having a flat bottom surface, and exposed to irradiation of actinic light having a wavelength of 300 to 400 nm for 3 minutes from above and below the Petri dish. A granular fixed yeast having a compression strength of 20 kg/cm$^2$ was obtained.

In a molasses culture medium, the resulting granular fixed yeast was examined for its ability to ferment an alcohol. It was found that its ability to ferment an alcohol was equivalent to non-fixed *Saccharomyces cervisiae*.

EXAMPLE 2

Distilled water (100 parts by weight) was added to 100 parts by weight of a photocurable prepolymer composed of 1,000 g of polyethylene glycol 2000 (molecular weight 2,000) and 2 moles of methacrylic acid, and the mixture was heated to about 50° C. and well mixed to form a uniform aqueous resin solution. Then, 2 parts by weight of benzoin ethyl ether was added and mixed.

To the resulting resin solution were added 75 parts by weight of a 3% aqueous solution of κ-carrageenan and 25 parts by weight of a cell suspension (concentration 10%) of *Saccharomyces carlsbergensis* (ATCC 9080) to form a uniform mixture. When the uniform mixture was added dropwise to a 5% aqueous solution of potassium chloride by means of an injection syringe from a position 20 cm above the liquid surface, a granular product having a particle size of 1.5 mm was obtained.

The granular product together with the potassium chloride solution was transferred to a Petri dish having a flat bottom surface so that it formed a single layer. The inside of the Petri dish was adjusted so that the granular product existed in the aqueous solution with a depth of 2 mm. Then, actinic light having a wavelength of 300 to 400 nm was irradiated onto the granular product for 3 minutes from above the Petri dish and for another 3 minutes from below the Petri dish. A granular fixed yest having a compression strength of 30 kg/cm$^2$ was obtained.

The resulting granular fixed yeast had a sufficient ability to ferment alcohol, and could form more than 10% of ethanol.

EXAMPLE 3

One part by weight of benzoin ethyl ether was uniformly mixed with 100 parts by weight of a resin solution (solids content 50%) obtained by neutralizing with sodium hydroxide a photocurable resin (number average molecular weight of about 4,100; acid value 75) prepared by reacting 1 mole of Epikote 1001 (molecular weight about 900, epoxy equivalent about 475; a tradename for a product of Shell Chemical Co.) with 1.5 moles of adipic acid, esterifying the reaction product with 4.5 moles of succinic anhydride and reacting the ester with 2.75 moles of glycidyl methacrylate. Furthermore, 50 parts by weight of a 3% aqueous solution of sodium alginate and 1.0 part by weight (concentration 30%) of a paste of cells of *Saccharomyces robustus* (IFO 0224) were uniformly mixed with the above mixture to form a dispersion. The resulting dispersion was added dropwise to a 1.0M aluminum chloride solution from an injection syringe to form a spherical gel. The spherical gel was transferred to a Petri dish, and exposed to irradiation of actinic light having a wavelength of 300 to 400 nm for 3 minutes each from above and below the Petri dish. A spherical fixed yeast having a diameter of 3 mm was obtained.

EXAMPLE 4

Two parts by weight of benzoin isobutyl ether was uniformly mixed with 90 parts by weight of a resin solution (solids content 75%) obtained by neutralizing with potassium hydroxide a photocurable resin having a number average molecular weight of about 25,000 and composed of a copolymer of 300 parts by weight of ethyl acrylate, 100 parts by weight of methacrylic acid, 80 parts by weight of styrene, 20 parts by weight of Phosmer M (a tradename for methacrylate-type monophosphate produced by Yushi Seihin K. K.) and 50 parts by weight of glycidyl methacrylate. To the mixture were added 50 parts by weight of a 3% aqueous solution of sodium alginate and 50 parts by weight of a cell suspension (concentration 10%) of *Saccharomyces formosensis* (IFO 0216), and they were uniformly mixed. The resulting uniform resin solution was added dropwise to a 10% aqueous solution of ammonium alum placed in a Petri dish. The resin solution was gelled in a granular form. Actinic light having a wavelength of 300 to 400 nm was irradiated onto the granular gel for 3 minutes each from above and below the Petri dish. A granular fixed yeast having a diameter of about 2 mm was obtained.

EXAMPLE 5

Benzoin isobutyl ether (0.5 part by weight) was uniformly mixed with 100 parts of a 25% aqueous solution of a photocurable resin obtained by the addition of 1.0 mole of N-methylol acrylamide to 500 g of polyvinyl alcohol having a degree of polymerization of 1,500. Then, 100 parts by weight of a 3% aqueous solution of κ-carrageenan and 10 parts by weight of a cell suspension (concentration 10%) of *Zygosaccharomyces japonicus* (ATCC 11069) were mixed uniformly with the resulting mixture to form a dispersion. The resulting photocurable resin/yeast dispersion was fed to a rotating disc and scattered by its centrifugal force to drop the scattered particles onto a 0.5M solution of potassium chloride to gel them in a granular form. The granular gel was put into a Petri dish, and exposed to irradiation of light having a wavelength of 300 to 400 nm for 3 minutes each from above and below the Petri dish to obtain a fixed yeast having a particle diameter of 3 mm.

EXAMPLE 6

One hundred parts by weight of a photocurable prepolymer composed of 2,000 g of polyethylene glycol having a molecular weight of about 4,000, 1 mole (222 g) of isophorone diisocyanate and 1 mole (130 g) of 2-hydroxyethyl methacrylate was well mixed with 2 parts by weight of benzoin isobutyl ether and 100 parts by weight of distilled water. To the mixture were added 100 parts by weight of a 2% aqueous solution of sodium alginate and 100 parts by weight of an enzyme, invertase (concentration 0.1%), dissolved in 0.1M phosphate buffer (pH 5). All of these materials were thoroughly mixed and the resulting photocurable resin-enzyme mixture was added dropwise to a 1M calcium chloride solution through an injecting syringe from a height 10 cm above the liquid surface. A granular product having a particle diameter of about 2 mm was obtained.

The granular product was taken into a Petri dish having a flat bottom surface, and exposed to irradiation of actinic light having a wavelength of 300 to 400 nm for 3 minutes each from above and below the Petri dish to obtain a granular fixed enzyme having a compression strength of 20 kg/cm$^2$ The invertase activity of the granular fixed enzyme was measured using sucrose as a substrate. It was found to have a specific activity, relative to non-fixed invertase, of 65%.

EXAMPLE 7

Distilled water (100 parts by weight) was added to 100 parts by weight of a photocurable prepolymer composed of 1,000 g of polyethylene glycol 2000 (molecular weight 2,000) and 2 moles of methacrylic acid. They were heated to about 50° C. and well mixed to form a uniform aqueous resin solution. Two parts by weight of benzoin ethyl ether was dissolved in the aqueous solution.

To the mixed resin solution were added 75 parts by weight of a 3% aqueous solution of κ-carrageenan and 25 parts by weight of a 2% glucose isomerase cell suspension (sodium bicarbonate buffer pH 8) to form a uniform mixture. The uniform mixture was added dropwise to a 5% aqueous solution of potassium chloride through an injection syringe from a height 20 cm above the liquid surface to give a granular product having a particle diameter of 1.5 mm.

The granular product together with the potassium chloride solution was transferred to a Petri dish having a flat bottom surface so that it formed a single layer. The inside of the Petri dish was adjusted so that the granular product existed in the aqueous solution with a depth of 2 mm. Actinic light having a wavelength of 300 to 400 nm was irradiated onto the granular product for 3 minutes each from above and below the Petri dish to give a granular fixed enzyme having a compression strength of 30 kg/cm$^2$.

The activity of the granular glucose isomerase was measured at 60° C. in a sodium bicarbonate buffer at a pH of 8 using glucose as a substate. It was found to have a specific activity, relative to non-fixed glucose isomerase, of 80%.

EXAMPLE 8

One hundred parts by weight of a resin solution (solids content 50%) obtained by neutralizing with sodium hydroxide a photocurable resin having an acid value of 75 and a number average molecular weight of about 4,100 and obtained by reacting 1 mole of Epikote 1001 (a tradename for a product of Shell Chemical Co.; molecular weight about 900, epoxy equivalent about 475) with 1.5 moles of adipic acid, esterifying the resulting product with 4.5 moles of succinic anhydride and reacting the ester with 2.75 moles of glycidyl methacrylate was well mixed with 1 part by weight of benzoin ethyl ether. Furthermore, 50 parts by weight of a 3% aqueous solution of sodium alginate and 0.5 part by weight of cells of Arthrobacter simplex (ATCC 6946) treated with acetone were uniformly mixed with the resulting solution and dispersed. Then, the dispersion was added dropwise to a 1.0M aluminum chloride solution from an injection syringe to form a spherical gel. The spherical gel was transferred to a Petri dish, and exposed to irradiation of actinic light having a wavelength of 300 to 400 nm for 3 minutes each from above and below the Petri dish. A spherical fixed microorganism having a diameter of 3 mm was obtained.

EXAMPLE 9

Benzoin isobutyl ether (2 parts by weight) was uniformly mixed with 90 parts by weight of a resin solution (solids content 75%) obtained by neutralizing with potassium hydroxide a photocurable copolymer having a number average molecular weight of about 25,000 and derived from 300 parts by weight of ethyl acrylate, 100 parts by weight of methacrylic acid, 80 parts by weight of styrene, 20 parts by weight of Phosmer M (a tradename for methacrylate-type monophosphate made by Yushi Seihin K.K.) and 50 parts by weight of glycidyl methacrylate. The mixture was further uniformly mixed with 50 parts by weight of a 3% aqueous solution of sodium alginate and 50 parts by weight of a 0.5% aqueous solution of glucose oxidase dissolved in 0.1M acetate buffer (pH 5.6). The resulting mixed resin solution was added dropwise to a 10% aqueous solution of ammonium alum placed in a Petri dish through an injection syringe to form a granular gel. The granular gel was exposed to irradiation of actinic light having a wavelength of 300 to 400 nm for 3 minutes each from above and below the Petri dish. A granular fixed microorganism having a diameter of about 2 mm was obtained.

EXAMPLE 10

One hundred parts by weight of a 25% aqueous solution of a photocurable resin obtained by the addition reaction of 500 g of polyvinyl alcohol having a degree of polymerization of 1,500 and 1.0 mole of N-methylolacrylamide was uniformly mixed with 0.5 part by weight of benzoin isobutyl ether. Then, 100 parts by weight of a 3% aqueous solution of κ-carrageenan and 10 parts by weight of a cell suspension of *Escherichia coli* were uniformly mixed with the resulting mixture and dispersed. The resulting photocurable resin-cell mixture was fed onto a rotating disc and scattered by its centrifugal force. The scattered particles were allowed to fall onto a 0.5M solution of potassium chloride to form a granular gel. The gel was put in a Petri dish and exposed to irradiation of actinic light having a wavelength of 300 to 400 nm for 3 minutes simultaneously from above and below the Petri dish to give fixed microorganism cells having a particle size of 3 mm.

What is claimed is:

1. A liquid composition comprising (a) 100 parts by weight of a hydrophilic photocurable resin having a number average molecular weight in the range of from 300 to 100,000, at least two ethylenically unsaturated bonds per molecule, and a hydrophilic group selected from a hydroxyl group, a carboxyl group, a phosphoric acid group, a sulfonic acid group, an amino group and an ether linkage, (b) 0.01 to 10 parts by weight of a photopolymerization initiator, (c) 0.5 to 15 parts by weight of a water-soluble polysaccharide having a molecular weight in the range of from 3,000 to 2,000,000, a water solubility at 25° C. of at least 10 g/liter, and an ability to gel upon contact with at least one polyvalent metal ion, and (d) 0.001 to 50 parts by weight of an enzyme or microorganism strain.

2. A process for producing a granular fixed molded article of an enzyme or microorganism strain, which comprises adding dropwise a liquid composition comprising (a) 100 parts by weight of a hydrophilic photocurable resin having a number average molecular weight in the range of from 300 to 100,000, at least two ethylenically unsaturated bonds per molecule, and a hydrophilic group selected from a hydroxyl group, a carboxyl group, a phosphoric acid group, a sulfonic acid group, an amino group and an ether linkage, (b) 0.01 to 10 parts by weight of a photopolymerization initiator, (c) 0.5 to 15 parts by weight of a water-soluble polysaccharide having a molecular weight in the range of from 3,000 to 2,000,000, a water solubility at 25° C. of at least 10 g/liter, and an ability to gel upon contact with at least one polyvalent metal ion and (d) 0.001 to 50 parts by weight of an enzyme or microorganism strain, to an aqueous medium containing a polyvalent metal ion to gel the composition in a granular form, and then irradiating actinic light on the resulting granular gel to cure the photocurable resin in the granular gel.

3. The process of claim 2 wherein the photocurable resin (a) is selected from the group consisting of unsaturated polyesters having an acid value of 40 to 200, unsaturated epoxides having an acid value of 40 to 200, anionic unsaturated acrylic resins, cationic unsaturated acrylic resins, polyesters derived from polyethylene glycols and (meth)acrylic acid, urethanization adducts of polyethylene glycols and 2-hydroxethyl (meth)acrylate, unsaturated celluloses and unsaturated polyamides.

4. The process of claim 2 wherein the photocurable resin (a) cures to a substantially water-insoluble fixed resin when exposed to irradiation of actinic light having a wavelength of from about 250 to about 600 nm.

5. The process of claim 2 wherein the photocurable resin (a) is a polyester derived from polyethylene glycol and (meth)acrylic acid or a urethanization adduct of polyethylene glycol and 2-hydroxethyl (meth)acrylate.

6. The process of claim 2 wherein the water-soluble polysaccharide (c) is selected from the group consisting of alkali metal alginates, carrageenan, konjac mannan and pectin.

7. The process of claim 2 wherein the polyvalent metal ion is an alkaline earth metal ion.

8. The process of claim 2 wherein the microorganism strain is a yeast having the ability to ferment alcohols.

9. The process of claim 2 wherein the aqueous medium contains the polyvalent metal ion in a concentration of from 0.01 to 5 moles/liter.

10. The process of claim 2 wherein the actinic light has a wavelength in the range of about 250 to about 600 nm.

11. A granular fixed molded article of an enzyme or microorganism strain prepared by the process of claim 2.

12. The article of claim 11 which has a particle diameter of from about 0.5 mm to about 5 mm.

* * * * *